United States Patent
Johansson et al.

(10) Patent No.: US 8,268,915 B2
(45) Date of Patent: Sep. 18, 2012

(54) POLYMER TWO PHASE SYSTEM AND USE THEREOF

(75) Inventors: Hans O. Johansson, Lund (SE); James Van Alstine, Uppsala (SE); Rolf Hjorth, Uppsala (SE); Karol Lacki, Uppsala (SE); Emmanuel Macedo, Uppsala (SE); Gunnar Malmquist, Uppsala (SE); Jamil Shanagar, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 324 days.

(21) Appl. No.: 12/602,840

(22) PCT Filed: Jun. 16, 2008

(86) PCT No.: PCT/SE2008/000401
§ 371 (c)(1),
(2), (4) Date: Dec. 3, 2009

(87) PCT Pub. No.: WO2008/156410
PCT Pub. Date: Dec. 24, 2008

(65) Prior Publication Data
US 2010/0179252 A1    Jul. 15, 2010

(30) Foreign Application Priority Data
Jun. 19, 2007 (SE) .................... 0701539

(51) Int. Cl.
*C08L 89/00* (2006.01)
*C08L 31/00* (2006.01)
*C08K 5/06* (2006.01)

(52) U.S. Cl. .................. 524/24; 524/378; 524/556

(58) Field of Classification Search .......... 524/27, 524/378, 556, 24; 536/23.1
See application file for complete search history.

(56) References Cited

U.S. PATENT DOCUMENTS

| | | | | |
|---|---|---|---|---|
| 4,743,550 A | * | 5/1988 | Ananthapadmanabhan et al. | 435/220 |
| 4,756,834 A | * | 7/1988 | Muller et al. | 210/635 |
| 5,093,254 A | | 3/1992 | Giuliano et al. | |

FOREIGN PATENT DOCUMENTS

WO   WO 2004/020629   3/2004

OTHER PUBLICATIONS

V.Gupta et al. "Role of water structure on phase separation in polyelectrolyte-polyethyleneglycol based aqueous two-phase system", Polymer 43 (2002) 3387-339.*
V.Gupta et al. "Role of water structure on phase separation in polyelectrolyte-polyethyleneglycol based aqueous two-phase system", Polymer 43 (2002) 3387-3390.*
De Gennes, P., "Wetting: statics and dynamics", Reviews of Modern Physics, 57(3):827-863 (1985).
Gupta, V., et al., "Role of water structure on phase separation in polyelectrolyte-polyethyleneglycol based aqueous two-phase systems", Polymer, 43:3387-3390 (2002).
Rastogi, A., et al., "Characterization and Application of a New Aqueous Two Phase System Based on Gum Acacia (ex. Acacia senegal), A Naturally Ocurring Polysaccharide and Polyethylene Glycol", Biotechnology Techniques, 3 (1):33-38 (1989).
Saravanan, S., et al., "Phase Equilibrium Compositions, Densities, and Viscosities of Aqueous Two-Phase Poly(ethylene glycol) + Poly(acrylic acid) System at Various Temperatures", J. Chem. Eng. Data, 51:1246-1249 (2006).

* cited by examiner

*Primary Examiner* — Michael M Bernshteyn

(57) ABSTRACT

The present invention relates to a liquid mixture comprising a first polymer, which is a poly(acid), a second polymer, which is a poly(ether), and at least one salt, wherein the molecular weight of the poly(acid) is in the range of 1000-100,000 Da. The second polymer is selected to be capable of forming immiscible aqueous phases in the presence of the poly(acid) and salt. The poly(acid) may be selected from the group consisting of poly(acrylic acid) and poly(methacrylic acid), and the second synthetic polymer may comprise ethylene oxide. The invention may be used for separation of biomolecules, cells or particles.

6 Claims, 6 Drawing Sheets

POLYMER TWO PHASE SYSTEM AND USE THEREOF

CROSS-REFERENCE TO RELATED APPLICATIONS

This application is a filing under 35 U.S.C. §371 and claims priority to international patent application number PCT/SE2008/000401 filed Jun. 16, 2008, published on Dec. 24, 2008, as WO 2008/156410, which claims priority to patent application number 0701539-9 filed in Sweden on Jun. 19, 2007.

FIELD OF THE INVENTION

The present invention relates to an aqueous liquid mixture, which comprises two or more polymers capable of forming a multiphase system wherein each phase is rich in one of the polymers. The invention also encompasses a method of isolating at least one target compound from a liquid using the multiphase system according to the invention as well as kits for carrying out such a method.

BACKGROUND OF THE INVENTION

The biotechnical revolution, including development of modern biopharmaceuticals and mapping of the human genome, has been made possible due to development of separation methods such as chromatography and electrophoresis. Such methods can be used in small scale as well as in large scale, and are known as flexible methods, being useful for a variety of substances including biological substances. However, they are demanding both technically and in terms of equipment. In addition, scaling of some processes such as electrophoresis results in a need for more complicated equipment due to nonlinear scaling of heating and cooling requirements.

Partitioning between the phases in aqueous polymer phase systems is an alternative method, which has been studied since the 1950's but whose commercial application has been severely restrained by lack of economically scalable phase systems. Together with separation methods such as crystallization and size exclusion; partitioning is considered a classic separation technique. It is related to differentially distributing a target and other substances between two phases. The term "partitioning" can refer to (a) liquid-solid partition such as in classic chromatography, (b) partitioning between two or more liquid phases (biphasic and multiphase system, respectively), (c) partitioning between a mobile liquid phase and another liquid phase immobilized at the surface of a solid phase support, and (d) partitioning of particles between a liquid phase and the phase interface between two phases. For the purposes of this patent application, partition and partitioning refer to situations such as b, c or d i.e. partitioning between liquid phases. Partition is typically expressed as a coefficient (K) related to the concentration in one phase versus another and for solutes K generally follows the Brønsted equation. Thus K is expected to vary exponentially with various types of interactions such as electrostatic and/or hydrophobic interactions, and also to be sensitive to solute size i.e. the area of interaction with liquid phases. In the case of interfacial partition, K is expected to vary exponentially with interfacial tension, which tends to localize particles to the phase interphase.

Classic two-phase systems are organic and aqueous two phase systems which normally have significant polarity differences between the phases, as well as significant interfacial tension. Such systems are not very useful for biologicals such as proteins or cells as they tend to be denatured by significantly apolar solutions and shear damage related to mixing of phase systems with significant interfacial tension. More useful for biologicals are the low tension, aqueous polymer two phase-systems. It is well recognized that the latter may contain some added organic solvents, e.g. ethanol, or other organic additives added to enhance target solubility, reduce liquid phase polarity, reduce foaming, act as bactericidal agents, etc.

Polymer two-phase systems can be formed by mixing certain hydrophilic and typically neutral polymers in aqueous solution. These include dextran (polyglucose) and poly(ethylene glycol) (PEG); as well as polysucrose (such as Ficoll™) and PEG; or linear polyacrylamide and PEG. Typical concentrations of each polymer are 5 to 10% w/w. At such concentrations, entropic forces tend to drive the formation of two phases both of which are typically greater than 90% (w/w) water but show subtle differences in polarity, hydrogen bond character, freezing point, etc. The phases are typically enriched in one polymer and have very low interfacial tension. In the biotechnical field, one advantage of the PEG and dextran type of two-phase system is that target proteins may partition in favour of the PEG-enriched phase while cell debris and some contaminants may partition to the interface or complementary phase.

WO 2004/020629 (Tjerneld) relates to the use of a PEG-like polymer comprising ethylene oxide (EO) groups in addition to propylene oxide (PO) groups, abbreviated as EOPO polymers. Such polymers, which show reverse thermal solubility, are known as "EOPO" polymers, and they are suggested in WO 2004/020629 for the separation of plasmids. At room temperature, the less dense, EOPO-enriched upper phase is isolated from the EOPO and dextran polymer aqueous two-phase system, and by a subsequent increase of its temperature to 37° C., the upper phase undergoes a further phase separation into a water-enriched phase and a self-associated EOPO polymer-enriched phase. Advantageously, the water-enriched phase should contain the desired plasmids. In general, this kind of EOPO and dextran systems offer advantages in terms of phase polymer component recycling and design of efficient two-stage partition separation process. However, a drawback is the cost involved in system formulation, which does not relate to the man-made synthetic polymer PEG but rather to the biologically derived and much more costly dextran.

Attempts to replace dextran with various starch or other polysaccharide polymers has resulted in limited success. One polymer, two-phase systems of intermediate interfacial tension can be formed by combining PEG and certain water structuring salts at relatively higher concentrations, e.g. 500 mM ammonium sulphate. PEG-salt two phase systems is one possible approach to overcome cost limitations but the increased PEG and salt concentrations create challenges which negatively impact process costs. These include viscous phases, salt reagent costs, salt disposal and equipment corrosion challenges, as well as target solubility issues which relate to capacity. As a consequence, the polymers are often difficult to recycle or otherwise have to be separated from the target via further downstream processing.

In the biotechnical field, polymer two phase systems, both in the forms with or without significant salt, are of general interest. This is because they are easily utilised in small as well as larger scale separations, without loss of efficiencies or dramatic changes in costs when scaling up to the larger volumes. Also, any standard separation approach, such as charge based, hydrophobicity based, affinity based, or size based separation, can be performed within a polymer two phase system. In general many undesired components, such as cell debris, endotoxins, nucleic acids will tend to appreciably partition to the lower (dextran-rich or salt rich, respectively) phase in a PEG and dextran or a PEG and salt two phase system. Thus, if a system can be found which provides for good target partition into the upper (PEG-rich) phase an effective primary separation and target concentration can be obtained.

Further, in efforts to overcome drawbacks related to interfacing in standard chromatographic and/or filtration processing, and to overcome the limitations of a single theoretical partition step per unit operation liquid-liquid partitioning two phase systems such as PEG-dextran or PEG-salt have been adapted to chromatographic uses by immobilising one phase on a chromatographic or other solid support capable of preferentially wetting that phase. The complementary phase is then pumped through the column offering repeated opportunities for equilibration between the mobile and stationary phase. This was commercially exploited by W. Müller et al. at Merck Darmstadt in the 1980's.

U.S. Pat. No. 5,093,254 (Giuliano et al) relates to an aqueous two-phase protein partitioning system is disclosed which employs polyvinylpyrrolidone as the upper phase and maltodextrin as the lower phase and provides a low-cost system for protein partitioning. The system can also be employed with the amion derivatives of chlorotriazine dyes, which bind in a noncovalent manner to the PVP and serve as a ligand for the proteins to be separated. It is stated that an advantage of this system is its cost-efficiency, as the dyes can easily be bound to the polymeric phase, without having to carry out the chromatographic and solvent extractions necessary to form the covalent bond in the PEG/hydroxypropyl starch system of the prior art. However, a drawback is the possible carcinogenic effect of such dyes.

Albertsson (P.-A. Albertsson, Partition of Cell Particles and Macromolecules, 2nd Edn., Wiley Interscience, N.Y., 1971. Chapter 10 Phase Diagrams, pp. 250-313) discloses systems comprising PEG and Na Carboxymethyl group modified dextran (CMD). The drawbacks of the system described is that (a) the polymer still involves an expensive polysaccharide; (b) the polymer is then further chemically modified; (c) the high molecular weight (Mw 2 200 000) and the inherent phase viscosity noted; and (c) the relatively high concentrations of polymers required to form phases, which is expected to bind water molecules and reduce system protein solubility.

Gupta et al (Vandana Gupta, Sunil Nath, Subhash Chand in Polymer 43 (2002) 3387-3390: Role of water structure on phase separation in polyelectrolyte-polyethyleneglycol based aqueous two-phase systems) relates to a study of the phase separation behaviour of polyelectrolyte-polyethyleneglycol (PEG) based aqueous two-phase systems (ATPS) carried out in order to elucidate the mechanism controlling phase-behaviour. Gupta uses polyethyleneimine (PEI) with a number average molecular weight of 60 000; and polyacrylic acid (PAA) with an average molecular weight of 250 000). It was concluded from this study that salt-assisted polymer-modified water structure interactions play a central role in phase separation in ATPS.

Saravanan (Settu Saravanan, Johny A. Reena, Jonnalagadda R. Rao, Thanapalan Murugesan, and Balanchandran U. Nair in J. Chem. Eng. Data 2006, 51, 1246-1249: Phase Equilibrium Compositions, Densities, and Viscosities of Aqueous Two-Phase Poly(ethylene glycol)+Poly(acrylic acid) Systems at Various Temperatures) relates to a study of the effect of temperature on the densities and viscosities of aqueous solution of poly(acrylic acid) (PAA) of different mass fraction (from 0.05-0.50) and liquid-liquid equilibrium, densities, and viscosities for the aqueous two-phase PEG-6000+PAA+water system at equilibrium.

As such there is still great need for novel separation methods, which are relatively technically simple and readily scaled.

BRIEF DESCRIPTION OF THE INVENTION

One aspect of the present invention is to provide a method of separating biomolecules and other compounds, which provides high dynamic capacities and fast mass transfer. As defined in the appended claims, this may be achieved according to the present invention by partitioning said biomolecules and/or compounds into a volume, and not to an insoluble porous matrix whose surfaces provide for capture of target via controlled adsorption.

Thus, a specific aspect of the invention is to provide such a method that works also with colloidal particles, such as cells, chromosomes, etc., which are not amenable to chromatographic or filtration approaches where the solid support interferes or becomes clogged. This can be achieved by using specific polymer two phase systems according to the invention.

An additional aspect of the invention is to provide the use of such a polymer two phase system for the separation of biomolecules and other compounds, which system forms and phase separates spontaneously, and preferably also requires little complex equipment.

Another aspect of the invention is to provide a polymer two-phase system as such, which system has been optimised in terms of additives such as salt for efficient separation of biomolecules.

A further aspect of the invention is to provide a use of such a two-phase system as well as a kit comprising the optimised two-phase system according to the invention.

One or more aspects of the invention may be achieved as defined in the appended claims. Further objects and advantages of the present invention will appear from the detailed disclosure that follows below.

DEFINITIONS

Figure 1:
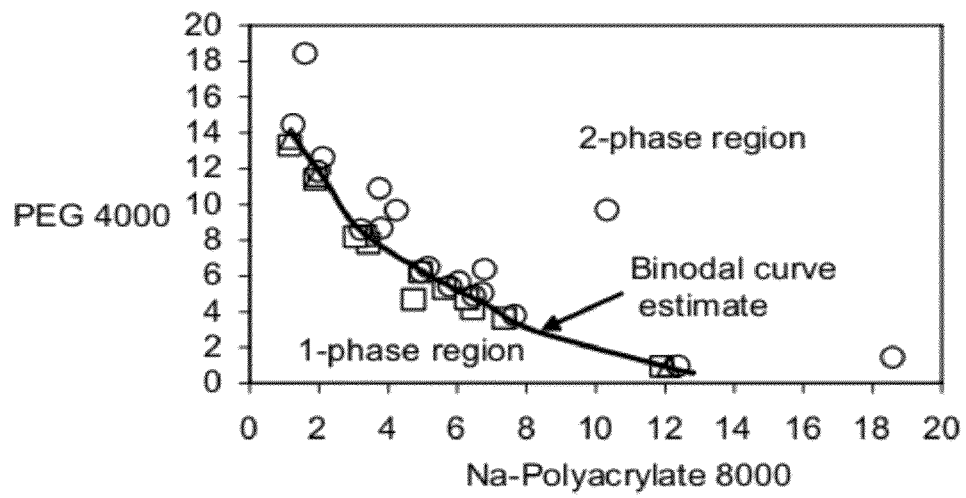
FIG. 1 is a phase diagram for aqueous polymer two-phase systems of the present invention formed using PEG 4000 and NaPolyacrylate 8000, which is the sodium form of polyacrylic acid polymer. More specifically, the system was formed with 200 mM NaCl at 22° C. Binodal curve was estimated visually by titration of the system to concentration points related to circles: two-phase systems; squares: one-phase systems; and triangles: systems apparently at bimodal region and difficult to assign. The present phases form at relative low (total) polymer concentration and they are clear, of relatively low viscosity, and separate rapidly at unit gravity. Furthermore the phase binodal curve is more linear near the critical point, suggesting that two-phase system formed near this region will have significant tie-line length and therefore be more reproducible in terms of physical properties and also in terms of partition results. Note that the lowest total polymer concentration on the bimodal polymer concentration on the bimodal curve appears at approximately 12%, corresponding to 6% of each polymer.

The term "poly(acid)" as used in the present application means a linear or branched poly(acid) backbone containing a multitude of acidic groups as side groups and/or end groups.

The term "target compound" means herein compounds as well as molecules and cells, i.e. any entity which it is desired to isolate from a liquid.

DETAILED DESCRIPTION OF THE INVENTION

The present invention relates to a liquid mixture capable of forming an aqueous polymer multiphase system, which comprises a first polymer, which is a synthetic poly(acid), a second synthetic polymer, which is a hydrophilic poly(ether), and at least one salt, wherein the molecular weight of the poly(acid) is in the range of 1000-100,000 Da.

The polymers used in the liquid mixture and multiphase system according to the present invention are aqueous in the sense that they form aqueous phases when combined with water. Further, as understood by the skilled person, in the present context the term liquid "mixture" refers merely to a combination of the herein-defined components. Under which conditions such liquid mixtures exist as one, two or more phases is deducible from phase diagrams. One advantage of the liquid mixtures of the invention is that they give rise to phases which appear less viscous, optically clearer and faster separating than many commonly studied phase systems.

The poly(acid) may be any suitable poly(acid). Thus, the backbone may be a hydrocarbon chain, a poly(ether), a polyester, a polyamide, a polyacetal, a polyurethane or a polysulfone. In one embodiment, the poly(acid) is a hydrocarbon (vinyl polymer) or a poly(ether) chain. The skilled person can easily prepare such poly(acid)s.

Thus, in one embodiment of the present liquid mixture, the poly(acid) is selected from the group consisting of polymers formed using acid-functional monomers such as acrylic acid, methacrylic acid, itaconic acid, crotonic acid, maleic acid, fumaric acid, vinylbenzoic acid, acrylamidoglycolic acid, acryloyloxyethyl succinate, vinylsulfonic acid, styrenesulphonic acid, acrylamidomethylpropanesulfonic acid, vinylphosphonic acid etc. In an advantageous embodiment, the poly(acid) is poly(acrylic acid) (PAA) or polyacrylate. When used in a polymer multiphase system, the PAA rich phase will be clear, separate rapidly and exhibit lower viscosity than dextran-based systems. Liquid mixtures capable of forming PAA-based multiphase systems according to the invention are readily formed by combining e.g. 40% solutions of commercially available NaPAA with a ethylene oxide polymer and salt.

The poly(acid) may be in acidic, anhydride or deprotonated form, i.e. the salt form.

In one embodiment of the present liquid mixture, the molecular weight the poly(acid) polymer is in the range of 900-100,000 Da, such as 1000-20,000 Da. In one embodiment, the molecular weight is in the broad range of 400-1,000,000 Da.

As the skilled person will understand, the present synthetic poly(acid) and poly(ether) are chosen to be able to form an aqueous two phase system in the presence of salt. The skilled person can easily deduce, based on phase diagram, at which pH values, salt concentrations, molecular weights etc the said polymers will exist in the system as one phase or as more.

Thus, in one embodiment of the present system, the poly(ether) is capable of forming a system of two physically different phases in the presence of the poly(acid) and salt, wherein each phase is enriched in one of the polymers.

In one embodiment of the present liquid mixture, the molecular weight the poly(ether) is in the range of 900-100,000 Da, such as 1000-20,000 Da. In one embodiment, the molecular weight is in the broad range of 400-1,000,000 Da.

In an advantageous embodiment, the poly(ether) is a synthetic polymer comprising ethylene oxide units. In an advantageous embodiment, the ethylene oxide polymer is selected from the group consisting of water soluble poly(ether)s which includes poly(ethylene)glycol (PEG); ethylene oxide propylene oxide (EOPO) in either random copolymer form (e.g. Breox® polymers) or block copolymers (e.g. Pluronic® polymers). As the skilled person in this field will realise, these polymers may include variously modified forms, such as. monomethoxy forms of PEGs.

In an advantageous embodiment, the ethylene oxide polymer is PEG. In the separation of biomolecules, PEG is often favoured by target localization as it is biocompatible and an accepted FDA excipient; and because it can be readily separated from proteins, cells and other targets.

In another advantageous embodiment, the ethylene oxide polymer is a ethylene oxide propylene oxide (EOPO). As is known by the skilled person, EOPO separates into two phases upon heating and is consequently regarded a thermoseparating polymer. Thus, in a specific embodiment, the ethylene oxide polymer is a thermoseparating polymer, such as EOPO. In this embodiment, the present system is capable of separating into three phases, which will be discussed in more detail below in the context of a method using the present multiphase system.

The total polymer concentration of the present liquid mixture can be optimised for each envisaged use. For example, it is well known that proteins and other macromolecules can be precipitated out of solution by addition of relatively high amounts of water soluble polymers. Therefore, if the system according to the invention is to be used in protein separation, too high a total polymer concentration would not allow for sufficient protein solubility to achieve a cost efficient separation. Thus, in one embodiment of the present liquid mixture, which is advantageous for the isolation of biomolecules and/or particles, the total polymer content constitutes about 8-20% (w/w) of the system. In one embodiment, the liquid mixture comprises 10-20% (w/w). In another embodiment, the liquid mixture comprises about 70% of water.

Thus, in one embodiment, the present liquid mixture comprises about 4-6% of each polymer, such as about 5%, about 4.5% or about 4% of each polymer. In another embodiment, the liquid mixture comprises up to about 10% of each polymer, such as about 8% of each polymer.

Thus, the skilled person can easily decide suitable conditions such as pH and temperature at which a multiphase system, such as a two phase system, is formed from the present liquid mixture based on phase diagram data and optionally very simple routine experimentation. In one embodiment, the pH value of the present liquid mixture is close to neutral. The temperature may be in the range of 4-30° C., such as room temperature, for forming a two phase system. If a third phase is to be formed from a thermoseparating polymer rich phase, then higher temperatures are used at that stage.

In a specific embodiment of the present system, the salt concentration is in the range of 1-500 mM, such as below 300 mM or in the range of 100-300 mM. As the skilled person will understand the amount of salt needed to form a two-phase system will be influenced by polymer MW, concentration and physical status. Thus only 100 mM buffer salt is required to form a two-phase system if it is formulated with the sodium or other salt form of the poly(acid).

In an advantageous embodiment, the salt is selected from the group consisting of NaCl, $Na_2PO_4$, $KPO_4$, $NaSO_4$, potassium citrate, $(NH_4)_2SO_4$, sodium acetate and combinations thereof. The skilled person can easily predict the effects of each specific salt on phase separation, such as the isolation of a protein, based on the Hoffmeister series. This because it is well known that salts at the lower end of the Hoffmeister series, such as NaCl, will tend to shift a net positively charged protein towards the ethylene oxide polymer rich phase; while a salt which is present more to the upper or right end of the Hoffmeister series instead will shift said protein towards the poly(acid) rich phase. In one embodiment, the present liquid mixture comprises 10% or less of salt(s).

In a specific embodiment, the present liquid mixture comprises one or more chromatography ligands. Such chromatography ligands may be used as a tool when applying the present liquid mixture to isolation of biomolecules or particles, in which case the ligands may bind a certain target compound partition said target compound to the phase favoured by the ligands. In one embodiment, the ligands are affinity ligands, which are capable of binding target molecules by highly specific interactions of the "lock/key" type, such as between receptor and ligand, or antibody-antigen. Illustrative affinity ligands are e.g. Protein A or Protein A-based ligands. In an advantageous embodiment, the affinity ligands are polymer-modified to facilitate their partitioning to a specific phase. In another embodiment, polymer-modified affinity ligands are added to partition interacting targets into the phase enriched in a polymer most similar to that linked to the ligand.

The two-phase systems formed from the liquid mixture of the invention which comprises ethylene oxide and acid-group containing polymers may contain other charged and non-charged groups, as is the case with two phase systems formed with PEG and poly(vinylmethylether-co-maleic anhydride) by the present inventors.

As the above discussed multiphase systems are useful for partitioning involves liquids, such a process can be readily coupled in line with other commonly used separation steps, from stacked disk centrifugation to chromatography and filtration. Accordingly, an advantageous use of the present invention is the separation of biomolecules or particles.

In a second aspect, the present invention relates to the use of a liquid mixture or multiphase system according to the invention in the separation of at least one target compound, such as a biomolecule, cell or particle. The target compound may be a protein, peptide, nucleic acid, cell, virus, or any part, fragment or fusion product of anyone of the above. Thus, in one embodiment, the target compound is an antibody, or a fragment or fusion product thereof. Illustrative antibody fragments are e.g. Fab fragments. In another embodiment, the target compound is a nucleic acid, such as DNA or RNA, e.g. a plasmid, genomic DNA, an aptamer or an oligonucleotide. In an additional embodiment, the target compound is a cell, such as a eukaryotic or a prokaryotic cell, for example an adult cell or a progenitor cell. In the present application, the term "particle" is sometimes used to denote a cell.

In a third aspect, the present invention relates to a method of isolating at least one target compound from a liquid, which method comprises (a) combining a synthetic polymer, which is a poly(acid), with a second synthetic polymer, which is a hydrophilic poly (ether), and at least one salt;

(b) adding a liquid comprising at least one target compound to the system obtained from (a);

(c) gentle mixing of the system obtained from (b) until at least two phases are formed; and, optionally, (d) recovering the desired target compound from one of the phases.

In one embodiment of the present method, in step (a), a liquid mixture according to the first aspect of the invention, as described above, is provided. Thus, in one embodiment, the molecular weight of the poly(acid) is in the range of 1000-100,000 Da.

In an advantageous embodiment, the hydrophilic poly (ether) is an ethylene oxide polymer. In a specific embodiment, in step (d), recovering the desired target compound from one of the phases, by a process which may involve allowing the formed phase regions (droplets) to coalesce into larger regions either spontaneously free in solution or aided by use of applied energy (centrifugation, electrophoresis, cooling) or aided by use of preferential wetting of one phase relative to the other on various surfaces (container, centrifuge, filter, particle, etc.)

In a specific embodiment, the present method involves a step of selecting a suitable balance between the polymer molecular weight and the pH versus the salt concentration, at which conditions a poly(acid) rich phase and phase rich of ethylene oxide polymer is formed.

As mentioned above, the poly(ether) is a thermoseparating polymer such as EOPO, and the liquid mixture according to the invention is then capable of forming three phases. In a first embodiment, the present method comprises forming the two phase system as described above, followed by removal of the poly(acid) rich phase before the phase which is rich in thermoseparating polymer, such as EOPO, is heated to provide a second two phase system from which target may be recovered.

However, the present inventors unexpectedly found that when the liquid mixture according to the invention is used to separate biomolecules, such as proteins, it is not necessary to remove the poly(acid) rich phase before subjecting the thermoseparating polymer rich phase to heating. Thus, in an alternative embodiment, the present method comprises heating of the two phase system until three phases are formed.

In one embodiment, in step (a), the polymer(s) has provided localized on a matrix or other surface via preferential wetting of the surfaces by one phase in the presence of the other phase. Such wetting phenomena are well known and include preferential wetting of natural surfaces, e.g. wetting of stainless steel or other metal or hydrophilic surfaces by the more polar poly(acid)-rich phase in the presence of the less polar PEG-rich phase. They can also include preferential wetting of less polar surfaces by the PEG-rich phase.

In another embodiment, single particles or aggregates of particles are used and said particles are typically less than 200 microns and greater than 5 nm in diameter.

The particles and/or aggregates may be covalently or otherwise modified with polymers; including use of various polymer modified "ligands" such as those commonly used in immuno-, lectin- or metal ion- or other-affinity chromatography, as well as ion exchange chromatography, hydrophobic interaction chromatography (HIC), and other modes of chromatography involving ion-pi, p-p and other interactions including those based on van der Waals or dispersion interactions.

In a fourth aspect, the present invention relates to a kit for the isolation of at least one target compound, such as a biomolecule, cell or particle, which kit contains a liquid mixture or multiphase system according to the invention, as described above.

In one embodiment of the kit, the liquid mixture or multiphase system is provided in a plastic bag. The different components of the kit may be presented in separate compartments of a container, such as a plastic bag. In an advantageous embodiment, the plastic bag is of a size that allows addition of a liquid from which one or more target compounds are to be isolated, and comprises means for addition of feed as well as means for mixing. In an advantageous embodiment, the present kit comprises at least polymer, which is a synthetic poly(acid), in aqueous solution or in dry form. The kit may comprises instructions, such as written or otherwise presented, for its use in the isolation of target compounds.

In a specific embodiment, the kit also comprises a second synthetic polymer comprising ethylene oxide, and at least one salt, wherein the molecular weight of the poly(acid) is in the range of 1000-100,000 Da.

EXAMPLES

The present examples are provided for illustrative purposes only, and should not in any way be construed as limiting the invention as defined by the appended claims.

Example 1

Preparation of Two Phase System According to the Invention and Phase Diagram

Materials

Polymers: Poly(ethylene glycols) 4000 (Merck), PEG 8000 (Sigma-Aldrich), Na-poly(acrylates) from Aldrich, CAS-number: 9003-04-7, Molecular weight 30000 (in 40 wt % water solution), Molecular weight 8000 (in 45 wt % water solution). NaCl and $Na_2SO_4$ Methanol, $Ba(NO_3)_2$ (from Merck and P.A. quality). Millipore water was used in all solutions.

Determination of Phase Diagram

The phase boundary of the stem (bimodal) was determined by the titration method well known methods [see Methods in Enzymology, Vol. 228, Aqueous Two-Phase Systems, Harry Walter and G. Johansson eds. Academic Press, New York, 1994]. In this case a system having a composition that is suspected to lie within the two-phase region is made. If the system turns turbid on mixing it indicates the existence of a two-phase system. Upon addition of a salt solution having the same salt concentration as the studied system the system becomes diluted with respect to the polymers. If the polymer concentration falls below a critical value the system turns into a one phase system, which does not become turbid on mixing. By adding polymers and diluting the system sequentially the phase diagram is mapped on both sides of the phase boundary, i.e. the binodal curve. The systems were determined in 22° C. (room temperature) and 25° C. (water bath).

Refractive Index Measurements

The refractive index of a solution is a linear additive property in water rich solutions (>90%). By making separate standard curves of known concentrations of PEG-water, Na-poly(acrylate)-water, and salt-water solutions. The refractive index instrument was obtained from Carl Zeiss (Oberkochen, Württemberg, Germany).

Determination of PEG

Since the solubility of salt and Na-poly(acrylate) is very low in methanol (<0.1 wt %) while PEG have a very high solubility, it is possible to selectively extract PEG into methanol and determine the PEG gravimetrically by evaporating the methanol. 1.00 g of a top or bottom phase is mixed with at least 6 g Methanol. A precipitate of Na-polyacrylate and salt is formed and is centrifuged at 3000×g for 10 min. The supernatant containing PEG is collected and placed in 15 ml glass tubes whose height are known. A further wash of the precipitate with 2 g Methanol with subsequent centrifugation is performed. This later supernatant fraction is pooled with the first one. The tubes are allowed to stay open in a vented hood for 3 days. Most of the Methanol is evaporated and the remaining is evaporated in an oven at 70° C. The tubes are weighed and the dried PEG is determined gravimetrically.

Determination of $Na_2SO_4$

The sodium sulfate salt can be determined by titration with Ba-sulfate. However, since the Na-polyacrylate is precipitated by divalent cations, this polymer must be removed before analysis. This is done by the following:

1 g sample (top- or bottom phase was added to a 15 ml glass tube (A). 0.1 g Na-polyacrylate 8000, (concentration: 45 wt % in water) and 0.3 g PEG 8000 (concentration 30 wt % in water) and 0.2 g HCL (37 wt %) was added to the sample and vortexed and finally centrifuged at 3000×g. A two-phase system was formed containing a bottom viscous phase composed by PEG and polyacrylic acid in high concentrations. The top-phase is a water rich phase. The volume ratio is high (>10). The water rich phase is collected carefully and placed in another 15 ml glass tube (B) with known weight. 1.5 g is added to the viscous phase in the glass tube (A) vortexed and centrifuged at 3000×g. The water rich phase is again carefully collected and placed in tube (B). In this procedure the PEG and polyacrylic acid is removed separated from the water solution containing all the $Na_2SO_4$.

1.5 g of warm 13 wt % $Ba(NO_3)_2$ water solution is now added to tube (B) containing sulfate salt and a precipitate of $BaSO_4$ is immediately formed. The tube (B) is centrifuged at 3000×g and the supernatant is discarded. This is repeated 3 times to remove traces of soluble material. The tube (B) with the $BaSO_4$ precipitate is dried in an oven at 70° C. 3 days. The amount of $BaSO_4$ is determined gravimetrically and the concentration of $Na_2SO_4$ can then be calculated.

Determination of Na-Poly(Acrylate)

The concentration of Na-polyacrylate is determined through refractive index (RI) by the following method. The RI of a phase that is diluted 3 times is determined. This value contains contribution from PEG and salt. From known concentration of PEG and Salt determined as described their contribution to the refractive index is determined. The resultant value is due to the Na-polyacrylate that is determined by the previously determined standard curves.

Phase Separation

The aqueous polymer phase systems are prepared according to standard for such systems. In order to get around the time needed for dry polymers to become fully hydrated, which in undisturbed solutions can take 24 hours, stock solutions of typically 30 to 40 weight % of the polymers are compounded. In the case of NaPAA it is possible to commercially purchase such stock solutions. In the case of PEG the stock solutions were compounded by the operator. So too stock solutions of NaCl (1 M) or other salts, e.g. 0.5M NaPhosphate pH 6.8, are also compounded. To make a 1000 gram (approximately 1 litre) phase system consisting of 6% PEG, 6% NaPAA, 300 mM NaCl, 50 mM NaPhosphate one simply mixes 150 g of PEG stock, 150 g of NaPAA stock, 300 g of NaCl stock and 100 g of NaPhosphate stock then adds water to the desired total. Once compounded such a system can be stirred for a few minutes to ensure full mixing and then allowed to spontaneously separate into two phases. To make 10 ml of the same system would simply require 100 times smaller amounts of each stock.

The two-phase systems are formed by mixing stock solutions of PEG, Na-poly(acrylate) and salt into 12 ml graded glass tubes. The total weight of the systems is 10 g. The systems are mixed up-side-down ca 15 times and the system becomes completely turbid. The system is then allowed to separate in a water bath at 25° C. The systems are generally completely separated within 30 min. However, the systems were allowed to stand for 1-2 hours. The refractive index of the phases is very similar so that it may be difficult to discover the interface. The separated phases are clear and have relatively low viscosity (visually observed).

Table 1 below provides information related to various tested PEG 4000 or 8000 and NaPAA 8000 or 30000 and NaCl or NaSulfate containing two phase systems. The PEG4000 and NaPAA 8000 two phase system at 22° C. is close to 5.28 and 5.68% respectively which is in keeping with the lower PEG polymer MW. By comparison, the PEG 4000 and NaPAA 30000 critical concentration is approximately 4.7 weight % of each polymer.

TABLE 1

PEG 4000 or 8000 and NaPAA 8000 or 30000 Two-Phase Systems*

| PEG | Na-poly(acrylate) | Salt type and concentration | Phase Separation noted after 2 hours at given temperature |
|---|---|---|---|
| Mw 4000, 4.7 wt % | Mw 30000, 4.7 wt % | NaCl 150 mM | ~22° C. Apparently at bimodal and close to critical concentration** |
| Mw 4000, 5.42 wt % | Mw 8000, 5.77 wt % | NaCl 200 mM | ~22° C. Two-phase system close the binodal (see FIG. 1) |
| Mw 4000, 5.28 wt % | Mw 8000, 5.68 wt % | NaCl 200 mM | ~22° C. One-phase system close to binodal |
| Mw 8000, 5.00 wt % | Mw 8000, 5.00 wt % | $Na_2SO_4$ 230 mM | 25° C. Two-phase system (see FIG. 2) |

*pH ~7.5, 1.05 wt % NaCl is approx. 150 mM, 3.00 wt % $Na_2SO_4$ is approximately 230 mM.
**Polymer concentration below this or salt concentration below this leads to system that does not appear to separate into two phases over two hour period.

Example 2

Effect of Salt and pH on Two Phase System According to the Invention

Two phase systems were prepared as described above. The effect of pH on EOPO 3900 and NaPAA 15000 systems was studied. The results are shown in Table 2 below which provides insight into the effect of pH on phase volume ratios and phase system formation in EOPO and NaPAA containing two-phase systems in 200 mM NaP buffer. At these polymer molecular weights, concentrations and salt conditions, two phases were formed at pH 6 to 8 but not at pH 5.

TABLE 2

Effect of salt and pH on EOPO 3900 NaPAA15000 two phase systems

| EOPO 3900 | PAA 15000 | mM NaP, pH 7 | Phase Forms | Volume Ratio | Upper EOPO-rich phase | Bottom NaPAA-rich phase |
|---|---|---|---|---|---|---|
| 4 | 4 | 0 mM pH 7 | – | | | |
| 4 | 4 | 100, pH 7 | – | | | |

TABLE 2-continued

Effect of salt and pH on EOPO 3900 NaPAA15000 two phase systems

| EOPO 3900 | PAA 15000 | mM NaP, pH 7 | Phase Forms | Volume Ratio | Upper EOPO-rich phase | Bottom NaPAA-rich phase |
|---|---|---|---|---|---|---|
| 4 | 4 | 200, pH 7 | + | 0.35 | clear | clear |
| 4 | 4 | 300, pH 7 | + | 0.28 | clear | Turbid |
| 4 | 4 | 400, pH 7 | + | 0.22 | clear | Turbid |
| 4 | 4 | 200 pH 5 | − | | | |
| 4 | 4 | 200 pH 6 | + | 0.35 | clear | clear |
| 4 | 4 | 200 pH 8 | + | 0.35 | clear | clear |

Example 3

Partitioning of Biomolecules in Polymer Two Phase System

Figure 2:
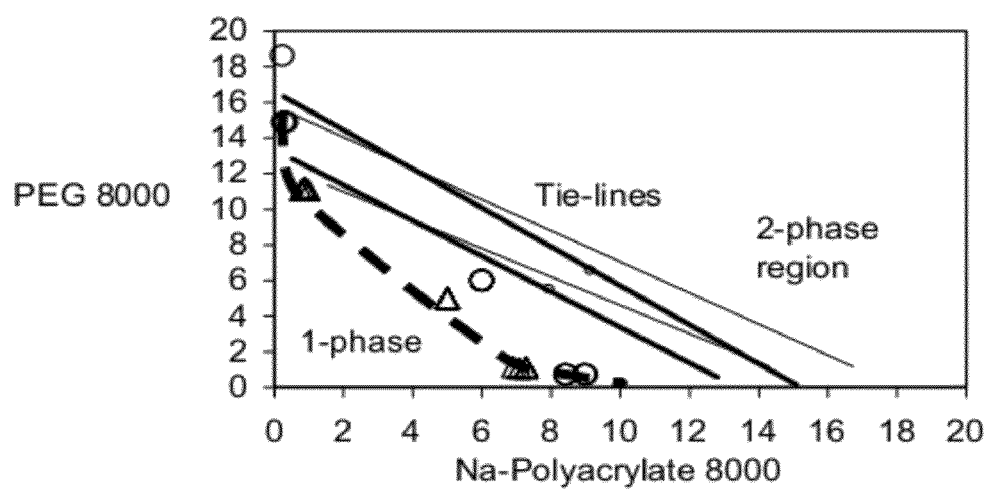
FIG. 2 is a phase diagram of a two-phase system according to the invention comprising PEG 8000 and Na-polyacrylate 8000, which is the sodium form of polyacrylic acid polymer. The diagrams refer to systems formed with approximately 230 mM Na$_2$SO$_4$ (3% weight) at 25° C. Phase compositions determined; (circles) two-phase systems, (squares) one-phase systems, (triangles) systems apparently at bimodal region and difficult to assign. The present phases form at relative low (total) polymer concentration and are clear, of low viscosity, and separate rapidly at unit gravity. Furthermore the phase binodal curve is more linear near the critical point, suggesting that two-phase systems formed near this region will be more reproducible in terms of physical properties and also in terms of partition results. Note that the lowest total polymer concentration on the bimodal curve appears at approximately 10%, corresponding to 5% of each polymer, which in comparison with FIG. 1 is in keeping with the greater water structuring effect of the sodium sulphate salt.
Figure 3:
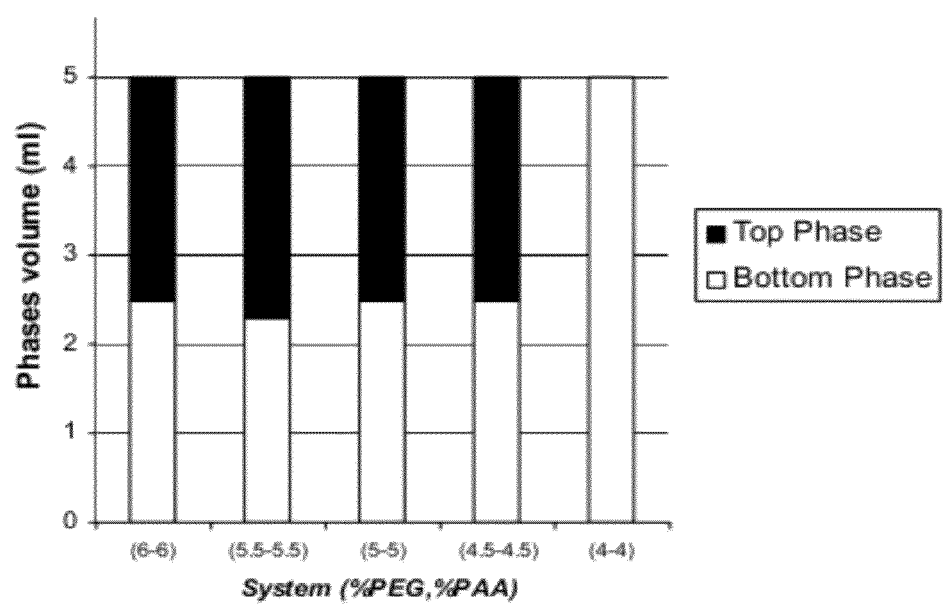
FIG. 3 is a diagram showing the distribution in a two-phase system according to the invention of PEG 8000 rich phase (top) and NaPAA 15000 rich phase (bottom) at room temperature in systems containing 200 mM NaSulfate, and adjusted to pH 7. Systems are denoted as (x-y) where x is PEG wt % and y is NaPAA wt %. In this case the critical concentration lies somewhere between 4% and 4.5% of each polymer which allowing for the greater phase forming capability of the higher MW NaPAA polymer and the lower temperature, compares reasonably well with FIG. 2. A phase system of approximately equal phase volume was achieved. Similar results were seen for systems containing NaPAA 8000 (not shown).

Plasmid DNA and RNA were partitioned in two phase systems according to the invention as follows: Partition results for pDNA and RNA were further verified by gel electrophoresis using a Phast® system, and DRIgest III® molecular weight standards (GE Healthcare) and published GE Healthcare protocols for such samples. Run times were 47 minutes for pDNA (FIG. 1, lanes 1-3) and 30 minutes for RNA (FIG. 1, lanes 4-6).

Figure 4:
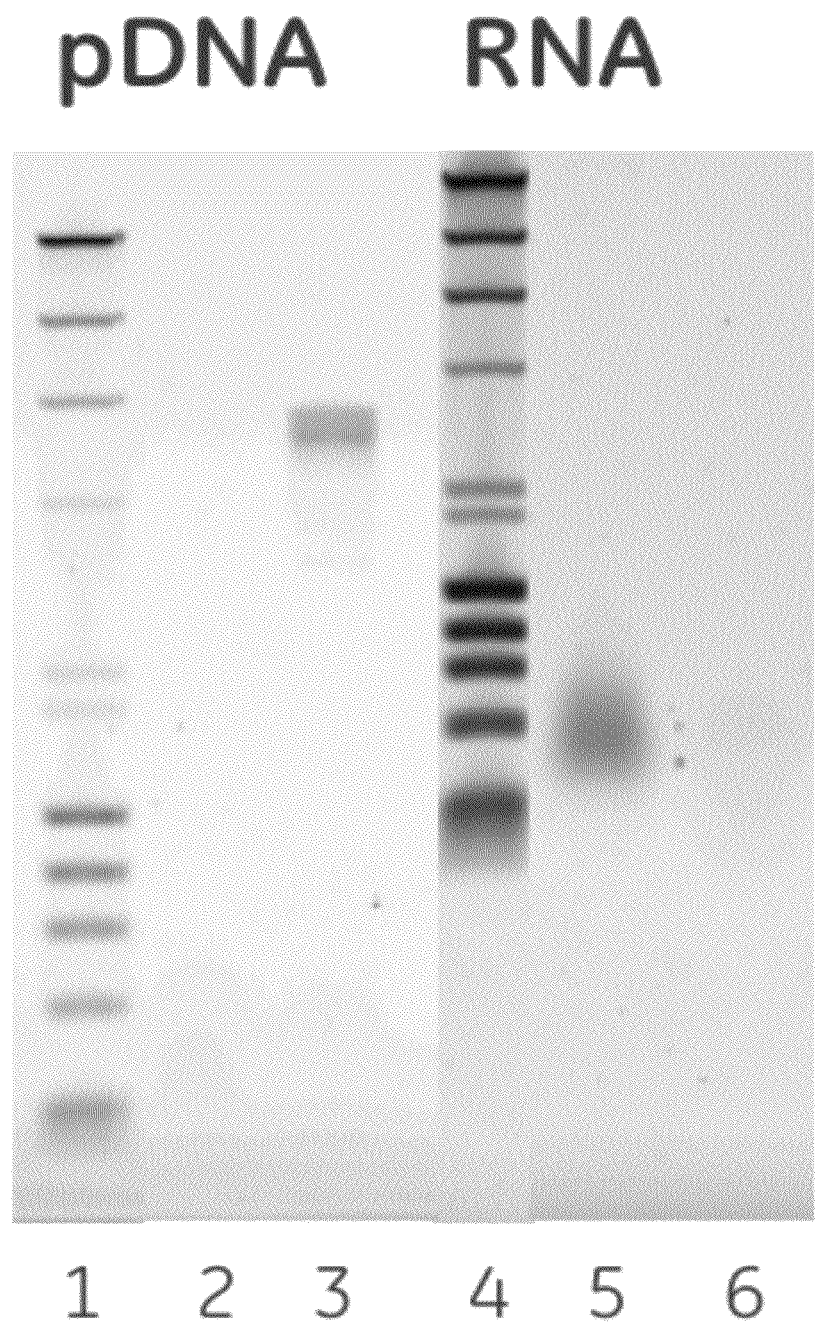
FIG. 4 shows electrophoretic analysis of phase system upper and lower phase samples for the plasmid DNA and RNA partition studies of Example 3 below. Electrophoresis of standards and upper and lower phase samples for the 6% PEG 8000, 6% NaPAA 8000, 3% NaSulphate, 10 mM NaPhosphate, pH 7 system in the above table. Lanes 1 to 3 are 47 min. runs for pDNA and lanes 4 to 6 are 30 minute runs for RNA. Lane assignments are: 1 MW standards, 2 Upper Phase, 3 Lower Phase, 4 MW standards, 5 Upper Phase, 6 Lower Phase.
Figure 5:
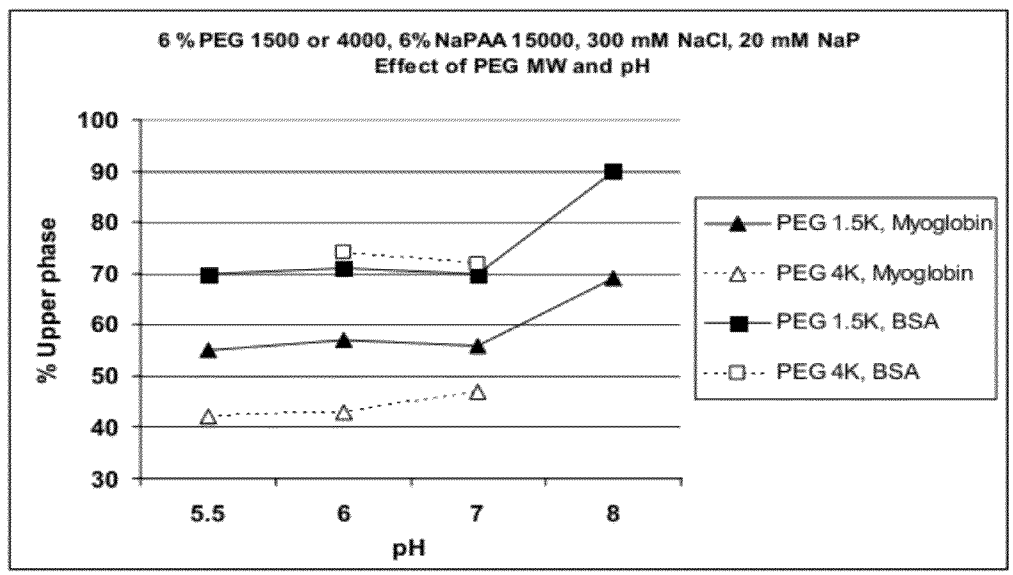
FIG. 5 illustrates the percent of model proteins myoglobin and bovine serum albumin (BSA) partitioning into the upper phase in systems consisting of 6% PEG 1500 or 4000 and 6% NaPAA 15000, 300 mM NaCl and 20 mM NaPhosphate pH 5.5 to 7.
Figure 6:
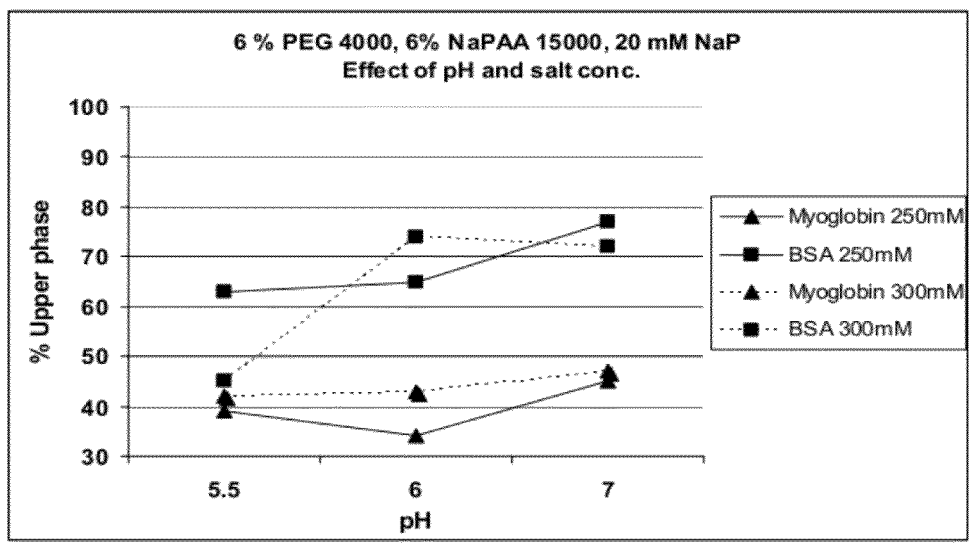
FIG. 6 illustrates the percent of protein partitioning into the upper PEG-rich phase in a system consisting of 6% (w/w) PEG 1500, NaPAA 15000, 20 mM NaPhosphate pH 6 or 8 and either 250 mM or 300 mM NaCl.
Figure 7:
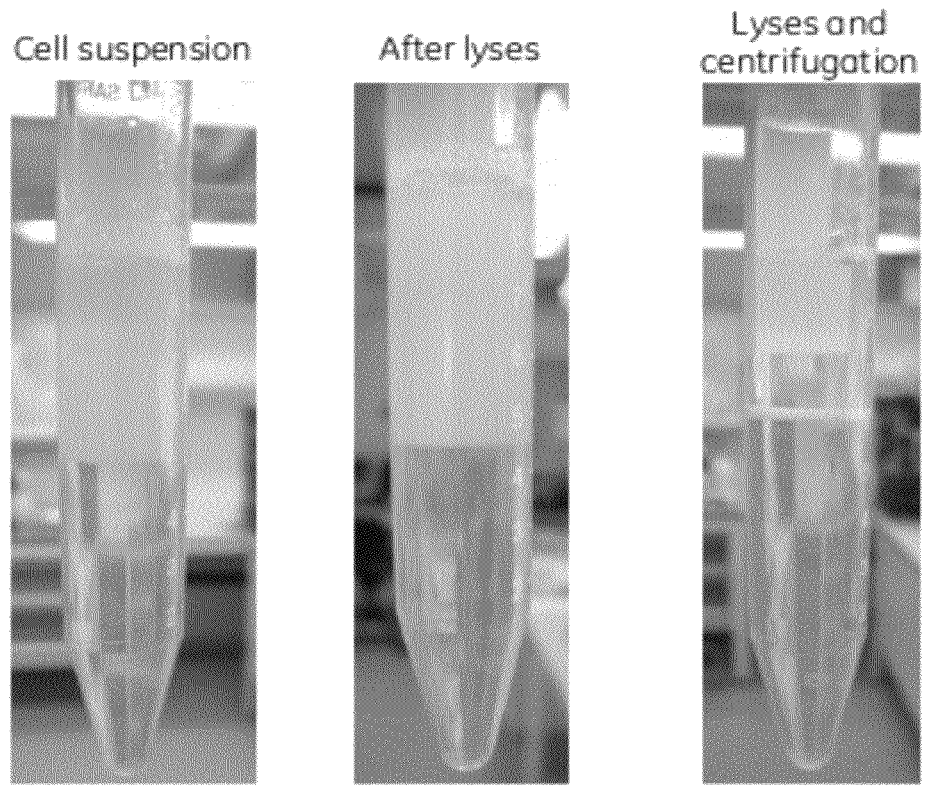
FIG. 7 is a series of three photographs illustrating the partitioning of *E. coli* cells which contain recombinant green fluorescent protein (GFP) in a two-phase system according to the invention comprising 6% PEG 8000, 8% NaPAA 15000 with 150 mM NaPhosphate pH 7. As appears from this figure, the intact cells partition to the upper PEG-rich phase, whereas the lysed cells partition to the upper phase, then after light centrifugation go to the interface. GFP, which is released from the lysed cells partitions with other released proteins somewhat in favour of the upper phase. This is seen by mildly centrifuging the tube to bring the lysed cells to the interface. These results indicate that for NaPAA based two-phase systems, specific phase systems can be found which are in the salt concentration range suitable for most cell partition, and that such systems may partition bacterial or other cells asymmetrically between the phases.

The results are presented in FIG. 4 and in the Table below.

TABLE 3

Single Step Partition of Plasmid DNA, RNA and model protein in various APTP systems according to the invention

| System Components 6% (w/w) PEG8000 plus | % pDNA Lower Phase | % RNA Upper Phase | % Protein Upper Phase |
|---|---|---|---|
| 6% NaPAA 8000, 3% NaPhosphate | 92 | 30 | 19 |
| 6% NaPAA 8000, 3% NaSulphate, 10 mM NaP | 89 | 64 | 9 |
| 6% NaPAA 15000, 3% NaPhosphate | 88 | 86 | 34 |
| 6% NaPAA 15000, 3% NaSulphate, 10 mM NaPhos. | 90 | 62 | 12 |
| 6% NaPAA 15000, 2% NaCl, 20 mM NaPhosphate | 90 | 50 | 100 | a. Polymer and salt composition given in % w/w. Systems were at 20° C. pH 7
The % partition results are mean values (X) typically based on n=3 experiments with typical SD of <0.1×.
b. Systems compounded using NaPAA 8000 45% (w/w) Sigma-Aldrich No. 416029 (Batch 12630LC) or NaPAA 15000 35% (w/w) Sigma-Aldrich No. 416037 (Batch 05206CA).
c. Systems evaluated using plasmid DNA (pDNA), RNA and test protein samples. Test protein was polyclonal human IgG sample (Gammanorm®, Octapharma).
The % partition results are mean values (X) based on n=3 experiments with typical SD of <0.1×.
d. Total amount of pDNA (pJV4 of 6 kbp) initially introduced into each tube ~0.25 mg (360 µl of 0.683 mg/ml stock solution U1504:100). Resulting total [pDNA]~0.05 mg/ml. RNA (U1489088) was initially dissolved in a 2.1 M $(NH_4)_2SO_4$ aqueous solution and required desalting using a PD-10 column (GE Healthcare Code No. 17-0851-01) prior to use. The desalted RNA stock of [RNA] ~0.16 mg/ml was added to each tube (386 µl of RNA stock solution, ~62.5 µg of RNA) to yield a total [RNA] per tube of ~0.025 mg/ml.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method of isolating at least one biomolecule or particle from a liquid, which method comprises
   (a) combining a first polymer, which is a poly(acid), with a second polymer, which is a hydrophilic poly(ether), and at least one salt, wherein the molecular weight of the poly(acid) is in the range of 1000-100,000 Da;
   (b) combining a liquid comprising at least one biomolecule or at least one particle with the system obtained from (a) to form a liquid mixture;
   (c) gentle mixing of the liquid mixture obtained from (b) until at least two phases are formed, wherein the liquid mixture comprises from about 4 to 6% of each polymer; and, optionally,
   (d) recovering the desired biomolecule or particle from one of the phases.

2. The method of claim 1, wherein the molecular weight of the poly(acid) ranges from about 1000 to 20,000 Da.

3. The method of claim 1, wherein the poly(ether) comprises ethylene oxide.

4. The method of claim 1, wherein in step (a), the polymer (s) has provided localized on a matrix via preferential wetting.

5. The method of claim 1, wherein
   said particle is a single particle or aggregates of particles and wherein said particle or the aggregates are greater than 5 nm and less than 200 microns in diameter.

6. The method of claim 5, wherein the particle and/or the aggregates are covalently modified with polymers.

* * * * *